US008190448B2

(12) United States Patent
Bajars et al.

(10) Patent No.: US 8,190,448 B2
(45) Date of Patent: May 29, 2012

(54) METHODS AND APPARATUS FOR HEALTHCARE SUPPLY PLANNING FOR HEALTHCARE CONTINUITY AND/OR PATIENT SURGE

(75) Inventors: Erika L. Bajars, Towaco, NJ (US);
Bridget C. Bagnato, Allendale, NJ (US);
Andrew R. Callison, Hoboken, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 695 days.

(21) Appl. No.: 11/948,135

(22) Filed: Nov. 30, 2007

(65) Prior Publication Data

US 2009/0144078 A1 Jun. 4, 2009

(51) Int. Cl.
*G06Q 50/00* (2012.01)
(52) U.S. Cl. ........................................................ 705/2
(58) Field of Classification Search .................. 62/127; 235/381; 705/2, 7, 10, 28; 706/50; 707/100
See application file for complete search history.

(56) References Cited

U.S. PATENT DOCUMENTS

| | | | | |
|---|---|---|---|---|
| 6,718,317 | B1 * | 4/2004 | Wang et al. | 706/50 |
| 7,111,780 | B2 * | 9/2006 | Broussard et al. | 235/381 |
| 2002/0174000 | A1 * | 11/2002 | Katz et al. | 705/7 |
| 2004/0260703 | A1 * | 12/2004 | Elkins et al. | 707/100 |
| 2005/0149379 | A1 * | 7/2005 | Cyr et al. | 705/10 |
| 2008/0147518 | A1 * | 6/2008 | Haider et al. | 705/28 |
| 2008/0184719 | A1 * | 8/2008 | Lowenstein | 62/127 |

OTHER PUBLICATIONS

FluSurge 2.0 Software to Estimate the Impact of an Infuenza Pandemic on Hospital Surge Capacity Manual Jun. 7, 2005.*
Becton, Dickinson, "BD FluStock Overview", *CDC FluSurge Program Brochure*, (2006),1-2.
Zhang, Xinzhi , et al., "FluSurge Software to Estimate the Impact of an Influenza Pandemic on Hospital Surge Capacity", www.cdc.gov/flusurge. (Jun. 7, 2005),1-16.

* cited by examiner

*Primary Examiner* — Gerald J. O'Connor
*Assistant Examiner* — John Pauls
(74) *Attorney, Agent, or Firm* — Jeanne P. Lukasavage; Deihl Servilla LLC (57) ABSTRACT

Methods and apparatus for determining a minimum recommended healthcare product supply to maintain a healthcare facility through a supply chain disruption, patient surge or a combination of both are described. Embodiments of the invention include the ability to make a combined list of healthcare products, minimizing the number of different healthcare products which are required to maintain a minimum inventory.

24 Claims, 8 Drawing Sheets

Number of weeks of inventory on hand for potential supply chain disruption: 4

| No. | Current Catolog Number | Current Annual Usage in Eaches | Description | Add'l Volume in Eaches | Recommended Catolog Number | Description |
|---|---|---|---|---|---|---|
| 1 | 301625 | 8,640 | 20 mL Slip Tip Syringe | 665 | 309653 | 60 mL Lure-Lok Syringe |
| 2 | 303345 | 11,100 | Blunt Plastic Cannula | 854 | 303345 | Blunt Plastic Cannula |
| 3 | 303367 | 37,000 | Vial Access Cannula | 2,847 | 305180 | Blunt Fill Needle, 18 G x 1 1/2 in. |
| 4 | | | | 2,847 | 303345 | Blunt Plastic Cannula |
| 5 | 303369 | 41,000 | Threaded Lock Cannula | 3,154 | 303370 | Lever Lock Cannula |
| 6 | 303370 | 669,400 | Lever Lock Cannula | 51,493 | 303370 | Lever Lock Cannula |
| 7 | 303401 | 568,800 | 3 mL Syringe with Interlink Vial Access Cannula | 43,754 | 309585 | 3 mL Lure-Lok Syringe |
| 8 | | | | 43,754 | 305180 | Blunt Fill Needle, 18 G x 1 1/2 in. |
| 9 | | | | 43,754 | 303345 | Blunt Plastic Cannula |
| 10 | 303405 | 380,000 | 10 mL Syringe with Interlink Vial Access Cannula | 29,231 | 309604 | 10 mL Lure-Lok Syringe |
| 11 | | | | 29,231 | 305180 | Blunt Fill Needle, 18 G x 1 1/2 in. |
| 12 | | | | 29,231 | 303345 | Blunt Plastic Cannula |
| 13 | 305106 | 16,000 | Needle, 30 G x 1/2 in. | 1,231 | 305760 | Eclipse Needle, 25 G x 5/8 in. |
| 14 | 305109 | 2,700 | Needle, 27 G x 1/2 in. | 208 | 305760 | Eclipse Needle, 25 G x 5/8 in. |
| 15 | 305122 | 14,200 | Needle, 25 G x 5/8 in. | 1,093 | 305760 | Eclipse Needle, 25 G x 5/8 in. |
| 16 | 305127 | 4,600 | Needle, 25 G x 1 1/2 in. | 354 | 305763 | Eclipse Needle, 22 G x 1 1/2 in. |
| 17 | 305145 | 6,600 | Needle, 25 G x 1 in. | 508 | 305762 | Eclipse Needle, 23 G x 1 in. |
| 18 | 305156 | 6,300 | Needle, 22 G x 1 1/2 in. | 485 | 305763 | Eclipse Needle, 22 G x 1 1/2 in. |
| 19 | 305165 | 200 | Needle, 21 G x 1 in. | 16 | 305762 | Eclipse Needle, 23 G x 1 in. |
| 20 | 305175 | 40,300 | Needle, 20 G x 1 in. | 3,100 | 305180 | Blunt Fill Needle, 18 G x 1 1/2 in. |
| 21 | 305180 | 754,000 | Blunt Fill Needle 18 G x 1 1/2 in. | 58,000 | 305180 | Blunt Fill Needle, 18 G x 1 1/2 in. |

FIG. 8

METHODS AND APPARATUS FOR HEALTHCARE SUPPLY PLANNING FOR HEALTHCARE CONTINUITY AND/OR PATIENT SURGE

BACKGROUND

The present invention relates to methods and apparatus to help healthcare facilities plan for emergency situations.

The Centers for Disease Control and Prevention (CDC) has developed a publicly available software package for estimating the surge in demand for hospital based services during an influenza pandemic. This program, called CDC FluSurge, addresses the current capacity of existing durable equipment (i.e., regular beds, ICU beds, ventilators), and how these resources will be constrained as a result of a pandemic.

FluSurge is a spreadsheet based model which provides hospital administrators and public health officials an estimate of the surge in demand for hospital based services during the next pandemic influenza outbreak. FluSurge estimates the number of hospitalizations and deaths of a pandemic influenza (whose length and virulence are determined by the user) and compares the number of persons hospitalized, the number of persons requiring ICU care, and the number of persons requiring ventilator support during a pandemic with existing hospital capacity.

FluSurge is designed to estimate the patient surge in a geographic region of the country. It does not provide data for a specific healthcare facility. FluSurge requires the user to know the patient population, by age, without providing any means for estimating that number. FluSurge also requires the user to identify, and input, the inventory of their durable medical equipment. The output from FluSurge expresses an estimated number of admissions due to influenza, percentage of hospital capacity needed due to influenza, an estimated number influenza patients requiring durable medical equipment, the percentage of durable medical equipment needed for aforementioned influenza patients, and an estimated number of deaths on a weekly basis. However, FluSurge does not provide direction on what should be done to meet these needs. Furthermore, FluSurge only addresses the requirements of a patient surge due to an illness; it does not provide for the effect of a supply chain disruption.

If the nation's healthcare facilities are not prepared for an interruption in their supply chains and/or the rapid influx of patients due to a major illness or event, a major catastrophe could occur. New methods and systems that assist health care facilities in preparing for supply chain disruptions and/or rapid patient influx in situations noted above are needed.

SUMMARY

One or more embodiments of the present invention are directed to methods of preparing a healthcare facility for patient surge, a supply disruption, or both. In a specific embodiment, a method of preparing a healthcare facility for a supply of healthcare products using a computer program comprising preparing a list of healthcare products subject to a supply disruption, a patient surge, or both; entering into the computer program healthcare product categories required to meet the healthcare facility's needs during the supply disruption, the patient surge, or both; and obtaining from the computer program a recommended minimum healthcare product inventory required to support the healthcare facility during the supply disruption, the patient surge, or both.

The method may further include entering into the computer one or more of healthcare product categories, healthcare product stock keeping units (SKUs), and the healthcare facility's usage rate of healthcare product stock keeping units (SKUs) to obtain the minimum healthcare product inventory required to support the healthcare facility during the supply chain disruption. In one embodiment, the healthcare facility's usage rate of healthcare product SKUs is manually entered. In another embodiment, the healthcare facility's usage rate of healthcare product SKUs is obtained upon entry of an identification number for the healthcare facility.

In certain embodiments, the method may also include determining from the healthcare facility's usage rate of healthcare product SKUs to identify different healthcare product SKUs having redundant functions and wherein the minimum healthcare product inventory required to support the healthcare facility during the supply disruption excludes at least one healthcare product SKU having a redundant function. The method according to one or more embodiments may further include performing one or more of: obtaining a cost analysis of the recommended minimum healthcare product inventory; entering current healthcare facility inventory of supply chain healthcare products subject to supply disruption; and determining the difference between the recommended minimum healthcare product inventory and a current healthcare facility inventory of supply chain products subject to supply disruption, and obtaining a cost analysis of the recommended minimum healthcare product inventory required to bring supplies to the minimum level.

The computer program may be linked to the inventory system of the user, the pricing system of the healthcare product supplier and, optionally, automatically places an order for healthcare products to bring the inventory to the recommended minimum healthcare product level.

The method may further comprise entering assumptions related a patient surge due to a pandemic disease outbreak. The assumptions affecting patient surge levels may comprise one or more of total population of persons served by the healthcare facility, the number of beds in the healthcare facility, length of pandemic disease outbreak, and hospitalization rate of the population based upon the pandemic disease attack rate on the population. The method may further include obtaining from the computer program an estimate of the rate of increase in the number of patients admitted to the healthcare facility due to the pandemic disease outbreak. In at least one embodiment, the disease is influenza.

Other methods may be limited to preparing a healthcare facility for a supply chain disruption only, or for a patient surge only.

Another aspect of the invention pertains to a system to assist a healthcare facility in preparing for a supply chain disruption, a patient surge, or both. In one embodiment, the system comprises a computer executing one or more applications; a database comprising a list of healthcare products; and an interface to the one or more applications through which assumptions are entered into the one or more applications, wherein the one or more applications recommend a minimum healthcare product inventory for products within the database based on entered assumptions when the healthcare facility is involved in a supply chain disruption, a patient surge event, or both. In one embodiment, the database contains a list of products which are routinely used by the healthcare facility and/or are products used to treat a symptom and/or complications of a specific illness. In certain embodiments, one or more applications determines the minimum recommended inventory using one or more of healthcare product categories, healthcare product SKUs, a current inventory of healthcare products on hand at the healthcare facility, and the healthcare facility's usage rate of healthcare product stock keeping units (SKUs) to obtain the minimum healthcare product inventory required to support the healthcare facility during the supply chain disruption.

In other embodiments, the one or more applications determines the minimum recommended inventory using one or more of healthcare product categories, healthcare product SKUs, a current inventory of healthcare products on hand at the healthcare facility, and the healthcare facility's usage rate of healthcare product stock keeping units (SKUs); and one or more applications further determines from the healthcare facility's usage rate of healthcare product SKUs to identify different healthcare product SKUs having redundant functions, and wherein the minimum healthcare product inventory required to support the healthcare facility during the supply chain disruption excludes at least one healthcare product SKU having redundant function.

The system may include a computer having a processor and executing an application comprising an algorithm. The system can include a database comprising a list of healthcare products, an interface allowing a user to enter assumptions into the computer program and an algorithm for recommending a minimum healthcare product inventory for products within the database, when the healthcare facility is in a supply chain disruption and/or surge event.

BRIEF DESCRIPTION OF THE DRAWINGS

FIG. 7 is an example report generated by a computer program according to one or more embodiments of the invention.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

In accordance with one aspect of the present invention, methods, computer programs and systems are provided, which are utilized to plan healthcare product supply to a healthcare facilities. The methods, computer programs and systems are designed to aid healthcare facilities in the identification of critical medical supplies and estimating the appropriate inventory levels to adequately prepare for widespread illness or injuries. Various aspects of the invention address the two related, but separate, considerations for supply planning: healthcare continuity and patient surge.

According to one or more embodiments, the healthcare continuity planning scenario is designed to aid healthcare facilities preparing for a potential disruption in the supply chain and seeking to support their current healthcare demand in the event of a pandemic or any emergency crisis situation.

According to one or more embodiments, the patient surge planning scenario is designed to aid healthcare facilities in preparing for an increase in patients due to the symptoms/complications of a pandemic influenza, or other disease or illness.

Healthcare facilities using embodiments of the invention may receive customized reports to assist in their pandemic influenza, or other disease, preparedness efforts. A planning recommendation report on healthcare continuity and patient surge as well as an overall planning report may also be created. These reports may include the inventory volumes of the critical products necessary to maintain continuity and treat patient surge based on the user's selections.

Various aspects of the present invention provide functionality not previously available to healthcare facilities. For example, the program of the present invention, provide functionality that includes, but is not limited to, the healthcare facility continuity planning scenario, one or more algorithms to estimate the population served by the healthcare facility, assumptions related to the facility and product planning level, and reports that include specific new inventory levels for healthcare continuity and patient surge, both individually and combined.

Embodiments of the invention utilize data specific to a healthcare facility consumables supplies and subject to supply disruption to estimate the facility needs for healthcare continuity and patient surge. Existing product usage is referenced to create a minimalist formulary or list of critical supplies for which a hospital should increase inventories to meet the estimated healthcare continuity and patient surge needs.

According to one or more embodiments of the invention, a method of preparing a healthcare facility for a supply chain disruption is disclosed. Using a computer program, a list of healthcare products is prepared by selecting from a product list of healthcare products subject to a supply chain disruption. Assumptions affecting the maintenance of an adequate supply of healthcare products are entered into the computer program, either by the user or as pre-entered parameters. A recommendation of the minimum healthcare product inventory to support the healthcare facility during a supply chain disruption may be generated.

Other embodiments of the invention are directed toward methods for planning for a patient surge in a healthcare facility. A computer program is used to provide a list of healthcare products by selecting items from a healthcare product list. At least a portion of the healthcare product items may be selected for the treatment of symptoms and/or complications of a specified illness. Assumptions affecting the patient surge levels can be entered into the computer, either by the user or as pre-entered variables. A list of the minimum healthcare product inventory recommended to support the healthcare facility during a patient surge can be produced.

Further embodiments of the invention are directed to methods of preparing a healthcare facility for both a supply chain disruption and patient surge. A computer is used to build a first list and a second list. The first list comprises a list of healthcare continuity products, where the healthcare continuity products are selected based on typical usage by the healthcare facility. The second list comprises a list of surge preparedness healthcare products, wherein at least a portion of the products are selected to treat symptoms and/or complications of a specified illness. Assumptions affecting the maintenance of an adequate supply of healthcare products and patient surge levels are entered into the computer program. A recommendation of the minimum healthcare product inventory required to support the healthcare facility during a supply chain disruption and a patient surge event can be generated.

In additional embodiments, the assumptions affecting the maintenance of an adequate supply of healthcare products, either for supply chain disruption, surge preparedness or both, comprises a computer based estimation of the population served by the healthcare facility.

Some embodiments include the ability to obtain a cost analysis of the recommended minimum healthcare product inventory. In other embodiments, the current healthcare facility inventory of supply chain disruption healthcare products may be entered into the program, either manually or through an automated link with the facility inventory system. Further embodiments determine the difference between the recommended minimum healthcare product inventory and the current healthcare facility inventory of supply chain disruption products. A cost analysis of the recommended minimum healthcare product inventory required to bring supplies to the minimum level can be generated.

One or more embodiments of the invention have the computer program linked to the inventory system of the user and the pricing system of the healthcare product supplier. In detailed embodiments, the computer automatically places an order for healthcare products to bring the inventory to the recommended minimum healthcare product level. The specified illness according to one or more embodiments is influenza.

According to one or more embodiments of the invention, a computer system is utilized to plan supplies for a healthcare facility in the event of a patient surge, a supply disruption, or both. Accordingly, an individual, using an appropriate device for entry of information into a computer system, for example, a desktop personal computer, a portable computer, a tablet personal computer or a personal digital assistant would access a program on a computer. Typically, upon opening the program, the user would view a welcome screen. Thereafter, the user of the program would enter information pertaining to the healthcare facility. The information may be an identification number unique to the healthcare facility. The identification number may be an enterprise resource planning identification number, for example, a unique SAP number that identifies the healthcare facility, which may be a hospital. Then, the healthcare facility's periodic usage or consumption rate (e.g., weekly or annually) of healthcare products is either automatically provided or manually entered. The usage or consumption rate of products will usually be based upon catalog numbers or stock keeping units (SKUs) for individual products. The catalog numbers or SKUs may be grouped together in certain product categories. After entry of this initial information, the computer program will request entry of further information related to maintaining healthcare continuity due to a supply chain disruption scenario or maintaining an adequate supply of healthcare products due to a patient surge scenario, for example, due to a pandemic disease outbreak in the geographic area in which the healthcare facility is located. In one or more embodiments, assumptions and information related to both scenarios may be entered into the program.

Figure 1:
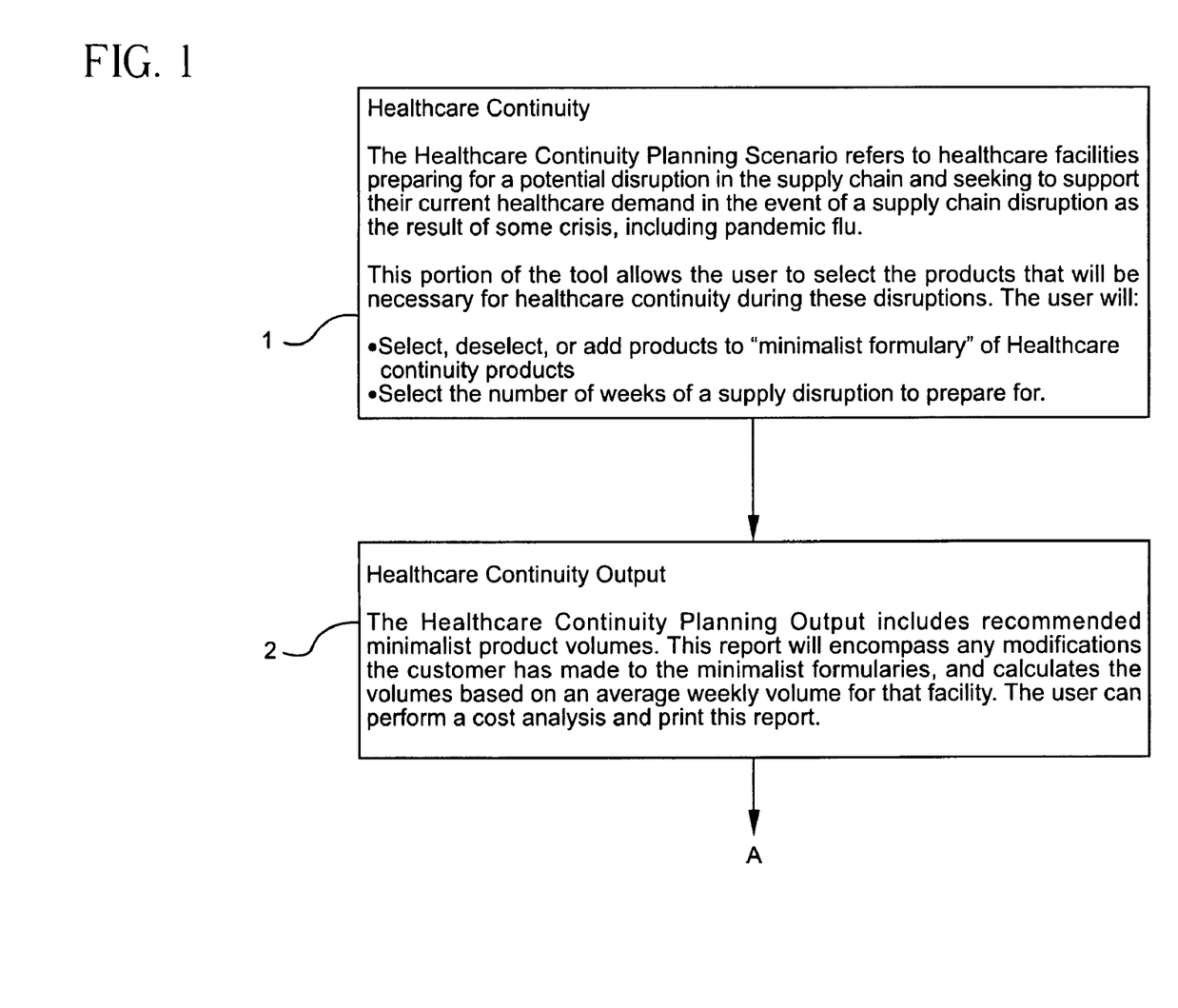
FIGS. 1 to 3 illustrate a flow chart in accordance with one aspect of the present invention.
Figure 2:
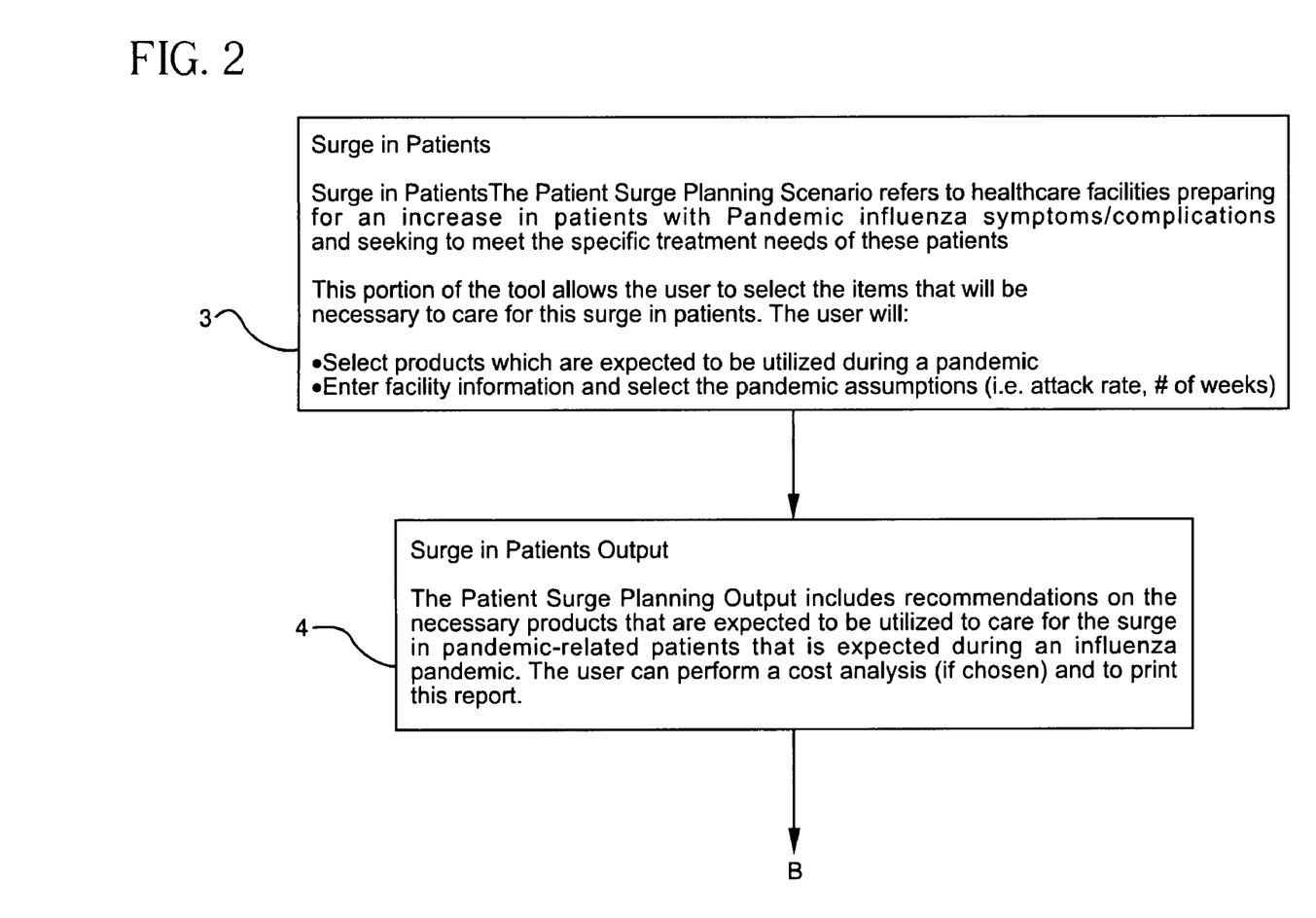
Figure 3:
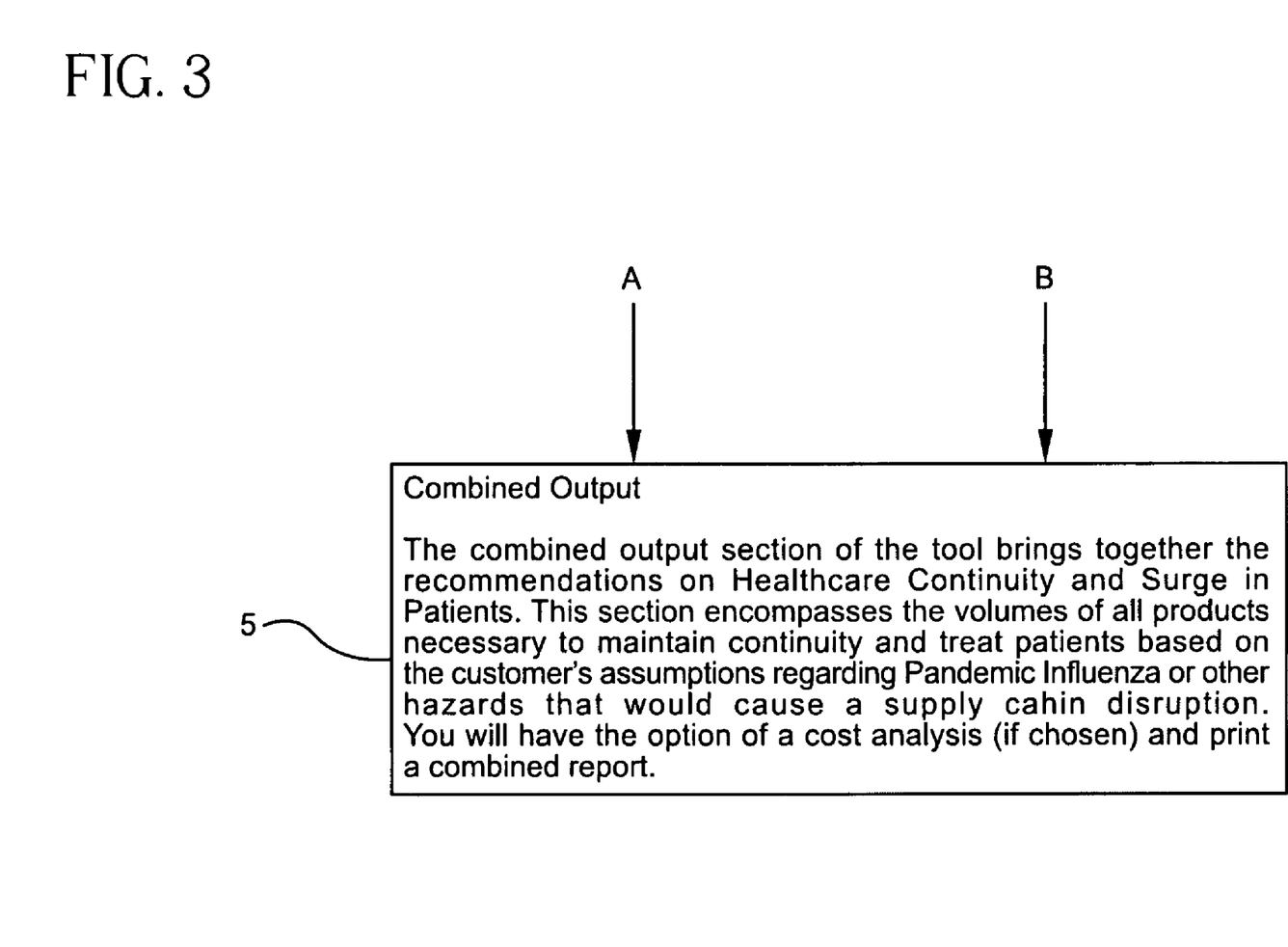

FIGS. 1 to 3 illustrate an embodiment of the present invention in greater detail. In FIG. 1, in step 1, a computer system is used to prepare for a potential disruption in the supply chain in the event of a pandemic. A user selects products from a list of healthcare products, typically based on product SKUs that will be necessary for providing health care during a disruption in the supply chain. The user can add, select or deselect the products from a database of products which has been manually entered or populated by the computer program based upon the healthcare facility identification number. The user can also select the number of weeks for which to prepare for a potential supply disruption.

In step 2, the computer program calculates a recommended minimum of product volumes that will be needed based on the assumptions entered. In accordance with one aspect of the invention, volumes are calculated based on a healthcare product usage rate, for example, an average weekly volume of use of the products for a particular facility. The computer program may determine from the healthcare facility's usage rate of healthcare product SKUs to identify different healthcare product SKUs having redundant functions and wherein the minimum healthcare product inventory required to support the healthcare facility during the supply chain disruption excludes at least one healthcare product SKU having redundant function. Optionally, a user can perform a cost analysis of ordering sufficient product to meet the recommended minimum products and can print the report. As another option, the healthcare facility may accept the recommended minimum healthcare product inventory, or it may add, delete or modify the recommended product catalog numbers or SKUs or units needed. The needed products can also be ordered.

In another embodiment, shown in FIG. 2, the computer program can determine products needed in the event of a patient surge, for example, due to a pandemic disease outbreak in the geographic area served by the healthcare facility. FIG. 2 shows that in step 3, which is not intended to be necessarily representative of a sequence of steps to those shown in FIG. 1, the computer programs calculates the products that would be needed in the event of a surge in patients from a pandemic event. An example of a pandemic event that can be planned for is the outbreak of influenza. In step 3, a user selects products that would be used during a pandemic and enters facility information such as, for example, the list of products shown in FIG. 7. As noted earlier, the products are typically listed by catalog or unique SKU number, and products may be grouped together into product categories. For example, certain product SKUs may be grouped under a product category labeled "catheters", while other product SKUs may be grouped into the category of "hypodermic" and subcategories of "skin injection" and "fill needle". The categories and subcategories may be utilized by the program in eliminating certain product SKUs from the recommended minimalist product volumes or minimum healthcare product inventory required to support the healthcare facility, particularly product SKUs having redundant product functions. The user also enters pandemic assumptions, which may include one or more of total population of persons served by the healthcare facility, the number of beds in the healthcare facility, length of pandemic disease outbreak, and hospitalization rate of the population based upon the pandemic disease attack rate on the population. This is discussed further below with respect to FIG. 5. The hospitalization rate assumption may be obtained from the CDC FluSurge program assumptions. These assumptions from the CDC FluSurge program may include, but are not limited to, death rate for non-hospitalized persons, death rate for hospitalized patients, risk of disease attack for certain population age categories and the hospitalization rate for each population age category.

In step 4, the computer program recommends the necessary products that will be needed during the pandemic event based on the assumptions entered in step 3. The user can perform a cost analysis associated with ordering the products that determined necessary and can print a report.

The steps illustrated in FIGS. 1 and 2 can be performed on the same computer by a single application. Alternatively, they can be performed on the same computer by a plurality of applications. Further, they can also be performed in a distributed computing system by a plurality of computers.

FIG. 3 illustrates a further embodiment of the present invention. Step 2 generates a first list of products that will be needed in a supply chain disruption. Step 4 generates a second list of products that will be needed in the event of a pandemic. These lists of products are combined in step 5 to produce a combined output listing needed products. A separate cost analysis can be performed on these products and a report can be printed.

As used herein, the term "healthcare facility" includes any place where people or animals are treated for injuries or illness. Examples of "healthcare facilities" include, but are not limited to, hospitals, nursing homes, hospices, physician offices, dialysis centers, clinics, surgery centers, diagnostic centers, triage centers, veterinary clinics and public health department locales.

As used herein, the term "healthcare product" includes any item used in a healthcare facility. Non-limiting examples of "healthcare products" include drugs (e.g., antibiotics, analgesics, nutritionals), devices (e.g., syringe pumps, syringes, gloves, scalpels) and cleaning supplies (e.g., sanitizing agents, towels, tissues). "Length of pandemic wave" refers to the period of time a pandemic illness outbreak affects the area served by a particular healthcare facility.

Figure 4:
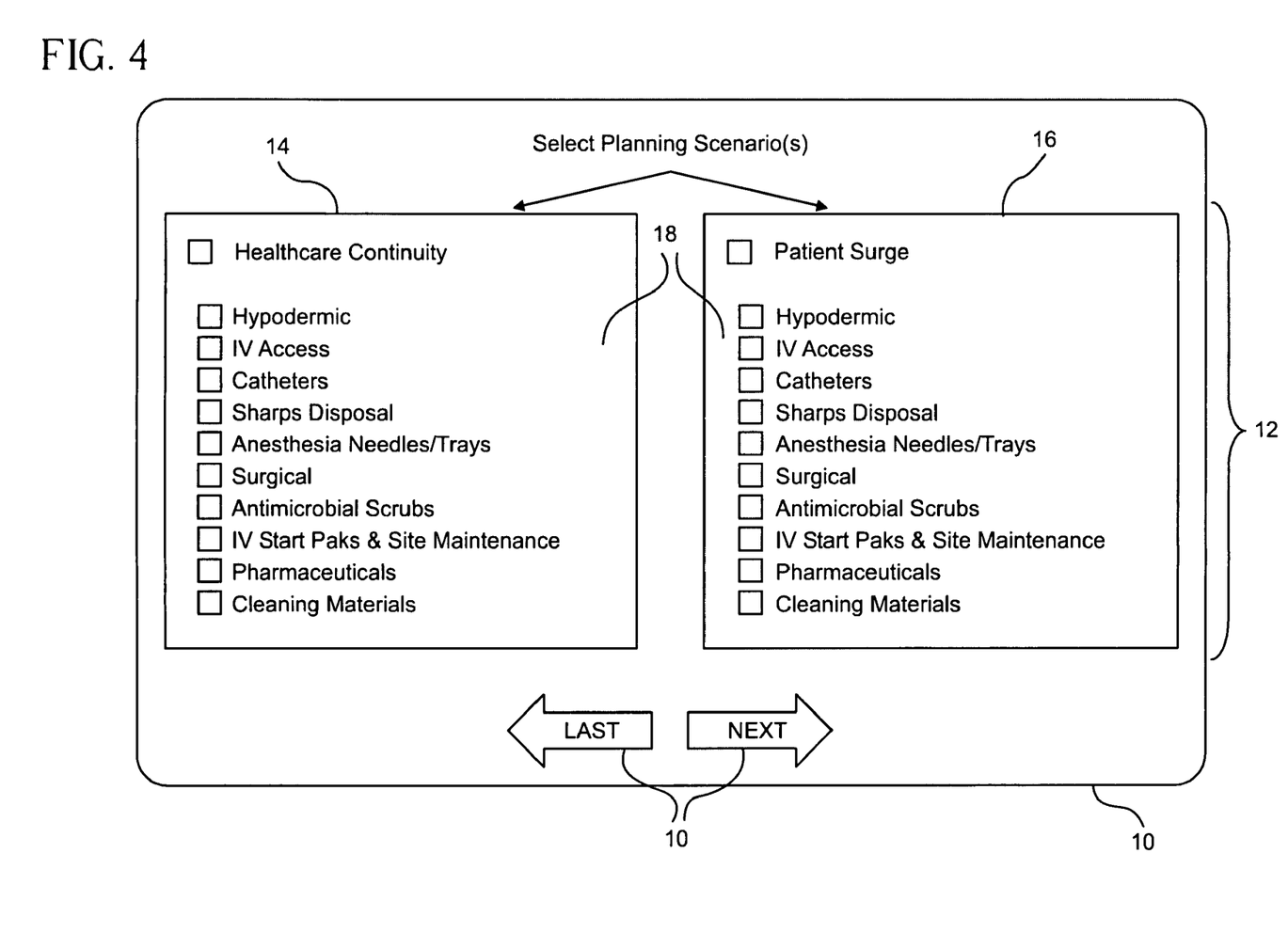
FIG. 4 is an example screen shot of a computer program according to one or more embodiments of the invention.

FIG. 4 shows an example of a decision screen 10 where a user would select the options 12 for analysis. The user can perform an analysis of a Healthcare Continuity scenario 14, a Patient Surge scenario 16, or both simultaneously. After selecting which scenario(s) will be analyzed, the user specifies the categories of healthcare products 18 which will be analyzed. The navigation buttons 20 allow the user to move to the next step or the previous step depending on the current place within the program. In FIG. 4 as displayed, a screen may precede this decision screen 10. The predecessor screen may include a place to enter preliminary information, for example, information about the person running the scenario, the facility being analyzed, etc.

Figure 5:
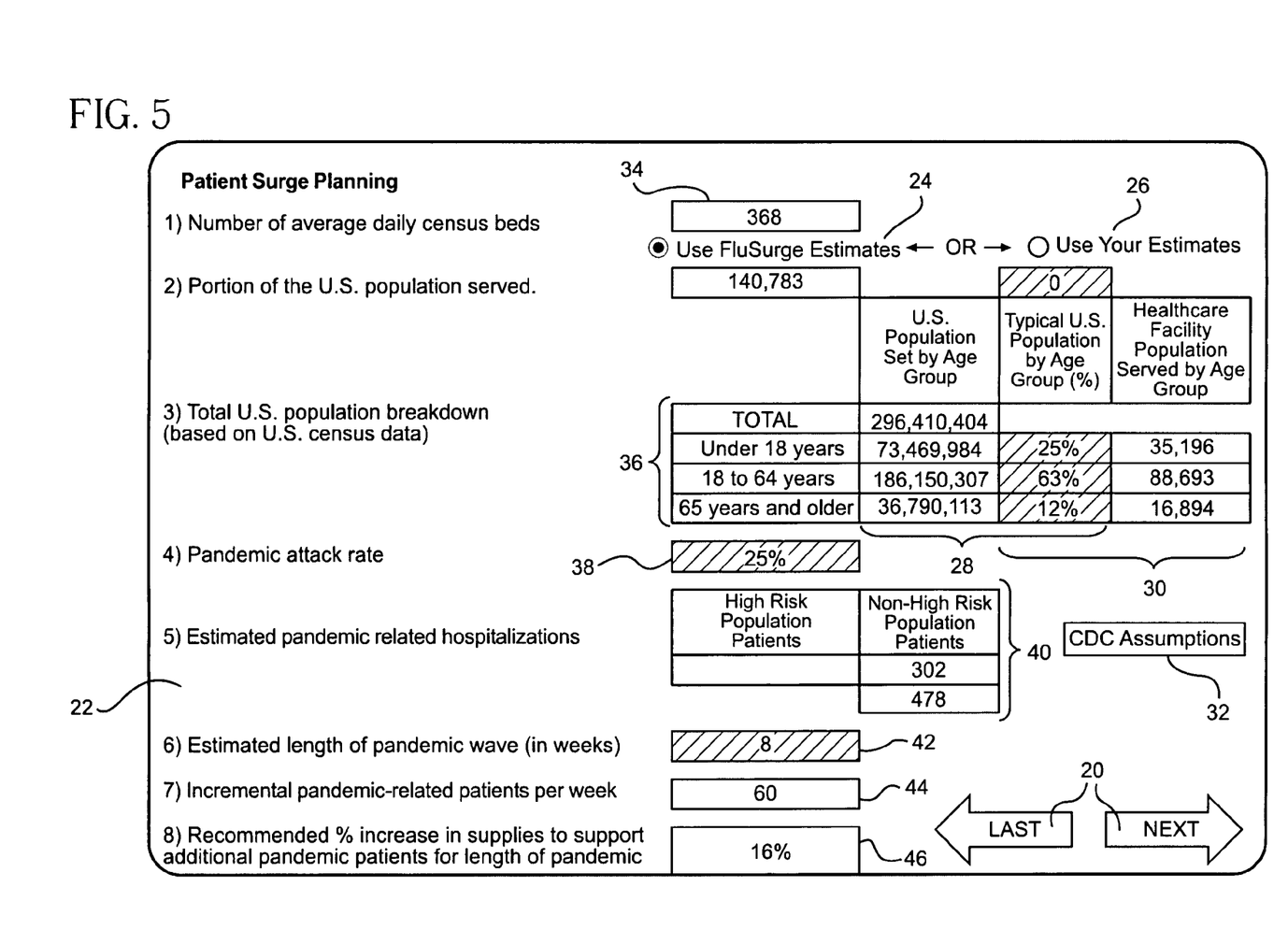
FIG. 5 is an example screen shot of a computer program according to one or more embodiments of the invention.

FIG. 5 shows an example screen shot 22 of the Patient Surge Planning scenario assumption screen according to various embodiments of the invention. The calculations can be based on the CDC FluSurge estimates 24 or custom estimates 26 based on the particular healthcare facility to determine the portion of the population served by the healthcare facility. The user enters the number of beds 34 available at the healthcare facility, the estimated pandemic attack rate 38 and the length of the pandemic 42. If no selection is made, the values for attack rate 38 and pandemic length will default to the CDC FluSurge default assumptions, which are 25% attack rate and 8 week pandemic wave. The user also has the ability to view or modify the assumptions used by the CDC assumptions 32. As noted above, the CDC FluSurge assumptions are obtained from the FluSurge program available from the CDC website, which include death rate for non-hospitalized persons, death rate for hospitalized patients, risk of disease attack for certain population age categories, and the hospitalization rate for each population age category.

The population demographics 36 for the calculations are displayed and can be modified for custom healthcare facility calculations, or be based upon CDC FluSurge estimates. When using the CDC FluSurge estimates, the program incorporates the U.S. population demographics 28 for the calculations to determine risk categories of the population, based upon age groups. When using custom estimates, custom demographics 30 can be set. The application can estimate the number of pandemic related hospitalizations 40, the incremental pandemic-related patients per week 44 and the recommended increase in supplies to support the healthcare facility 46. These values are estimates based on hospital input and CDC FluSurge assumptions of how many additional pandemic related patients per week the hospital will have and the percentage increase in supplies needed to support those patients. The user can navigate to previous pages or proceed with the displayed estimates by using the navigation buttons 20.

Figure 6:
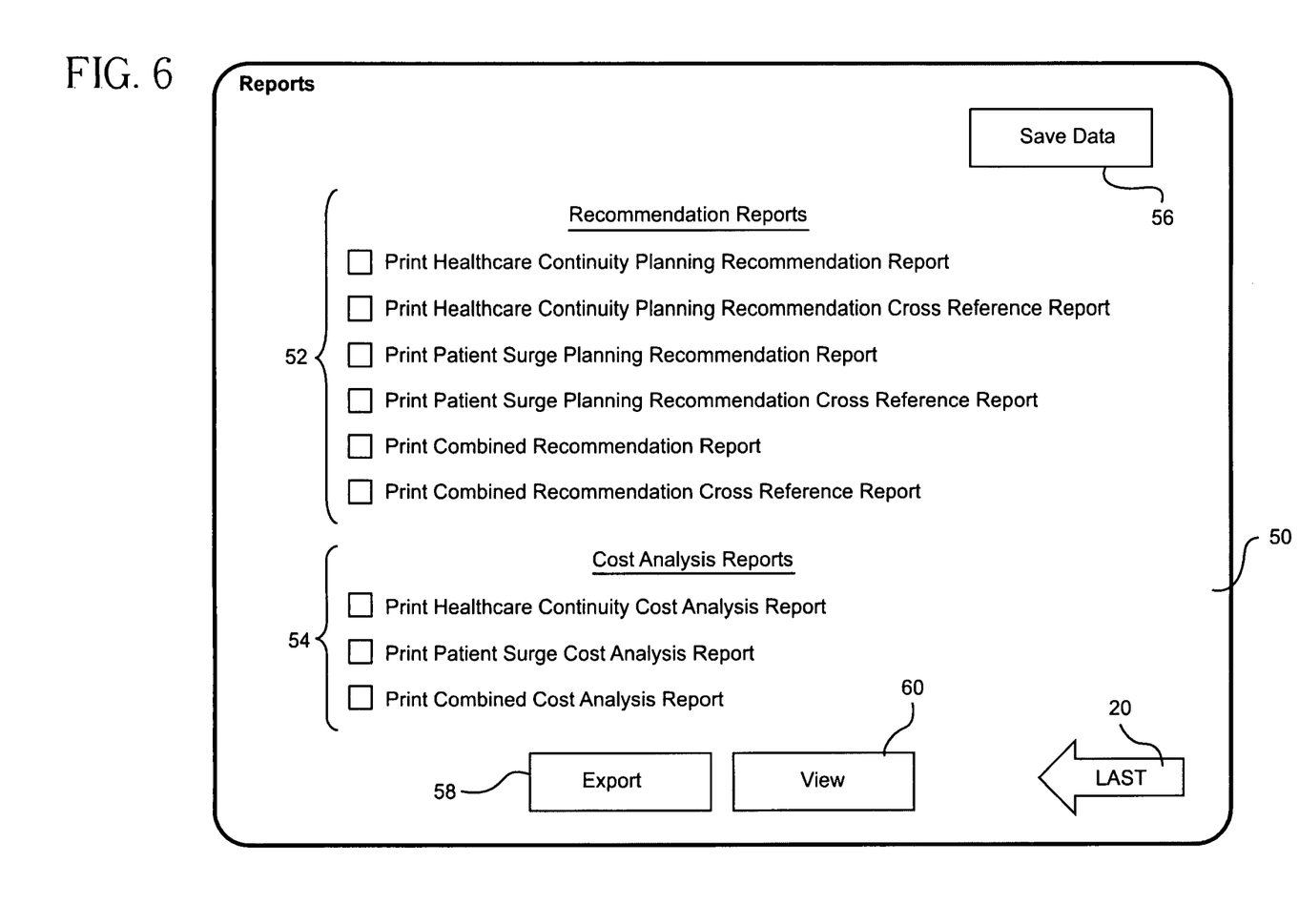
FIG. 6 is an example screen shot of a computer program according to one or more embodiments of the invention.

FIG. 6 is an example of a Reports page screen shot 50. The user can select which Recommendation Reports 52 and/or Cost Analysis Reports 54 are desired. The results can be exported 58 as various data types for use in other computer applications, or viewed 60 on the computer screen. The user can also save the data associated with the assumptions and the resultant reports by pressing the Save Data button 56. This allows the healthcare facility to rerun the scenario under different conditions without having to re-enter all of the assumptions. In the particular embodiment shown by FIG. 6, the Reports screen is the last screen. Thus, a navigation button 20 only allows the user to go back to the previous screen. In other embodiments, there can be additional screens or navigation buttons.

FIG. 7 shows an example Healthcare Continuity Planning Recommendation Report 62 according to one or more embodiments of the invention. The report displays information related to the current healthcare facility usage 64 and a recommendation of items to meet the facility requirements during a supply chain disruption 66. It is noted that a similar report (not shown) can be generated for a patient surge scenario discussed above. The current healthcare facility usage 64 of the embodiment shown includes the catalog number of each item 68, the number of units used annually 70 and a description of the item 72. The recommended information 66 includes the number of units which should be added to the inventory 74, the catalog number of the recommended items 76 and a description of the recommended item 78. The number of weeks chosen for a supply chain disruption 80 can be modified, thereby affecting the recommended items 66. A similar report can be generated for a patient surge scenario discussed above.

The recommended items 66 are not necessarily the same as the currently used items 64. Aspects of the invention substitute some products with comparable products to minimize the variety of items needed during the supply chain disruption preparation, in particular product catalog numbers or SKUs that have redundant functions. Referring to FIG. 7, the recommendation list, for example, does not include the same components as items 13 and 14. Instead, these items are replaced with a comparable product, which happens to be the same as item 15. Instead of having to order three different catalog items, the healthcare facility only needs to order one.

In some cases, multiple items are recommended to substitute for a single currently used item. Referring to FIG. 7, item number 3, it is recommended that a vial access cannula be replaced with a combination of a blunt fill needle and blunt plastic cannula. At first glance, it may appear that this adds an additional catalog item to be ordered, but that is not the case. There are sixteen individual items listed in the current healthcare facility usage 64, and a total of eight individual items on the recommendation list 66. By reducing the number of items, the ordering process is made easier because fewer line items need to be entered. It also makes storage of the items easier, because there is a smaller number of items to segregate in a storage closet.

In one or more embodiments, the computer program is linked to the inventory system of the healthcare facility and the pricing system of the healthcare products supplier. The computer program can, optionally, automatically place an order for healthcare products to bring the inventory level to the recommended minimum healthcare product level.

Other embodiments of the invention are direct toward apparatus to aid a healthcare facility in preparing for supply chain disruption and/or patient surge. The apparatus comprises a computer having a processor, the computer executing an application comprising an algorithm, a database comprising a list of healthcare products, an interface allowing a user to enter assumptions into the computer program and one or more algorithms for recommending a minimum healthcare product inventory for products within the database, when the healthcare facility is in a supply chain disruption and/or surge event.

The apparatus of other embodiments has a database which contains a list of products which are routinely used by the healthcare facility and/or are products used to treat the symptom and/or complications of a specific illness.

Further embodiments have an algorithm which determines the minimum recommended inventory using one or more healthcare product categories, healthcare product SKUs, a current inventory of healthcare products on hand at the healthcare facility, and the healthcare facility's usage rate of healthcare product stock keeping units (SKUs) to obtain the minimum healthcare product inventory required to support the healthcare facility during the supply chain disruption. In other embodiments, the algorithm determines the minimum recommended inventory using one or more using assumptions related a surge in patient demand due to a pandemic disease outbreak, the assumptions including total population of persons served by the healthcare facility, the number of beds in the healthcare facility, risk of hospitalization categories for the population, hospitalization rate for each risk of hospitalization category, length of pandemic wave, death rate for non-hospitalized persons, and death rate for hospitalized patients. One or more of these assumptions may be obtained from the CDC FluSurge program.

Other embodiments of the apparatus have the computer program linked to one or more of the healthcare facility inventory system and an ordering system of the healthcare products. The computer program of some embodiments automatically places an order for healthcare products to bring the healthcare facility inventory to the recommended minimum levels.

One or more embodiments pertain to an apparatus to aid a healthcare facility in preparing for a patient surge during an epidemic and/or a supply chain disruption. The apparatus comprising a computer having a processor. The computer executes at least two applications. The first application can be adapted to determine the level of patient surge during an epidemic, and the second application can be adapted to determine a minimum healthcare product inventory required to maintain adequate inventory during a supply chain disruption. The computer further comprises a database comprising a list of healthcare products routinely used by the healthcare facility and/or products used to treat the symptoms and/or complications of a specific illness. An interface allows a user to enter assumptions into the first application and the second application. The computer executes at least one algorithm for determining a minimum healthcare product inventory to maintain a healthcare facility through the patient surge, and at least one algorithm for creating a combined list of the minimum inventory of healthcare products from the recommendations of the first application and the second application.

Figure 8:
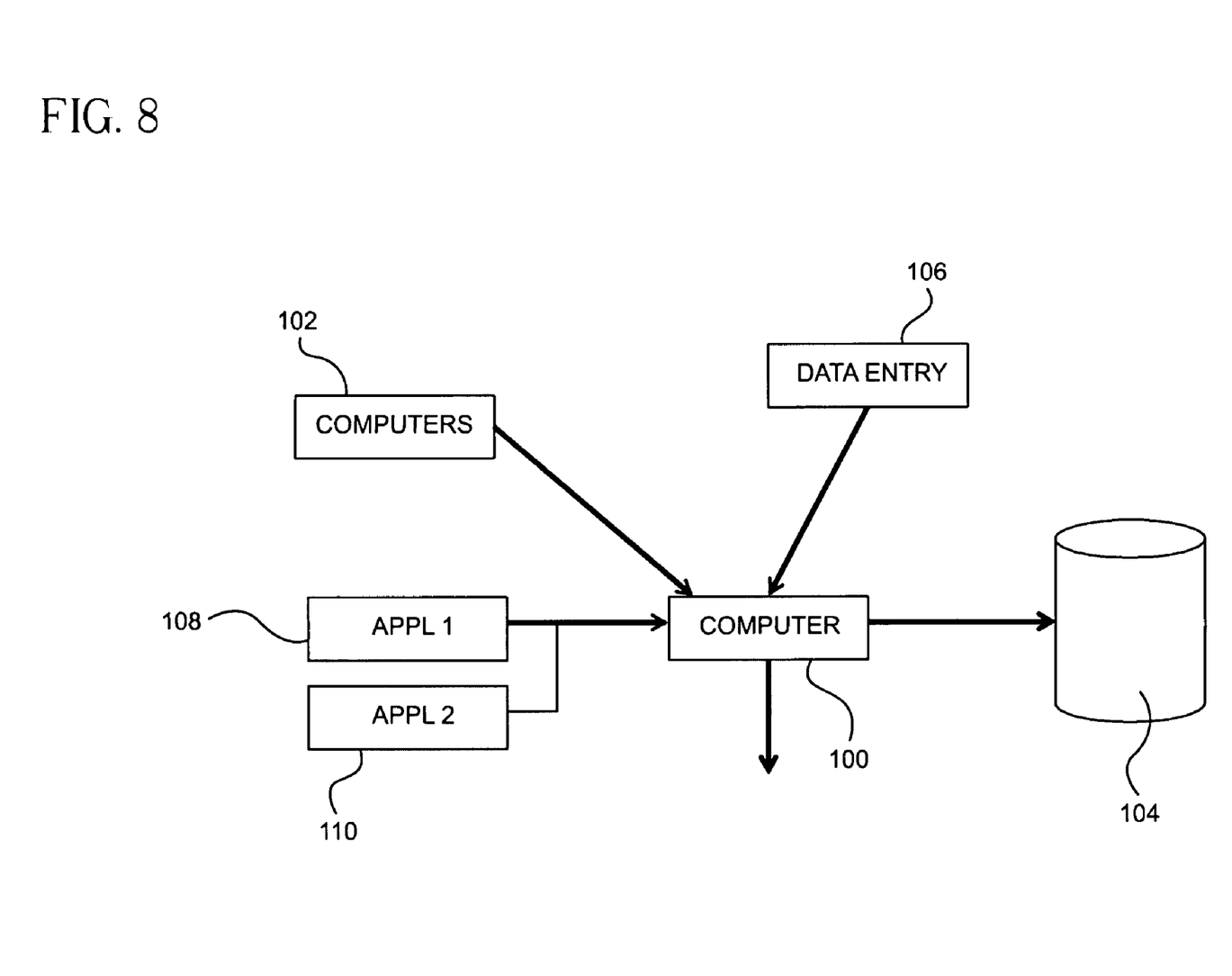
FIG. 8 illustrates a system in accordance with one aspect of the present invention.

FIG. 8 illustrates a computer system in accordance with one aspect of the present invention. A computer 100 can be a personal computer or any other computing apparatus, including portable devices. The computer 100 can be linked to other computers 102. As mentioned before, the computers 102 can be an inventory computer or a product ordering computer. In this way, the computer 100 can obtain information pertaining to inventories quickly or can automatically cause products to be ordered.

A database 104 or other memory device is connected to the computer 100 to maintain information about assumptions, products and any other information needed. A data entry 106 device, including a keyboard and a display, are provided to allow a user to enter the assumptions and any other information. One or more software applications 108 and 110 are loaded onto the computer 100 to provide the steps outlined herein.

Accordingly, while the present invention has been disclosed in connection with various embodiments thereof, it should be understood that other embodiments might fall within the spirit and scope of the invention, as defined by the following claims.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used in this specification and the appended claims, the singular forms "a", "an" and "the" include plural references unless the context clearly indicates otherwise.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

We claim:

1. A method of preparing a healthcare facility for a supply of healthcare products using a computer program executed by a computer having a processor, the method comprising:
providing in the computer program a first list comprising a list of pharmaceutical and non-pharmaceutical healthcare continuity products, wherein the healthcare continuity products are selected based on typical usage by the healthcare facility;
providing in the computer program a second list comprising a list of surge preparedness pharmaceutical and non-pharmaceutical healthcare products, wherein at least a portion of the surge preparedness healthcare products are selected to treat symptoms and/or complications of a specified illness;
on an input screen generated by the processor, providing to the computer program assumptions related to a potential supply disruption, the assumptions including an estimate of a population served by the healthcare facility and a period of time of the potential supply disruption;
on the input screen generated by the processor, providing to the computer program a set of assumptions relating to a patient surge, the set of assumptions including a pandemic disease attack rate a total population served by the healthcare facility, a hospitalization rate of the population based on the pandemic disease attack rate and a length of a pandemic disease outbreak; and executing the computer program using the computer to process the list of healthcare continuity products, the list of surge preparedness healthcare products and assumptions related to the supply disruption, the patient surge, or both, to obtain recommended minimum healthcare product inventory required to support the healthcare facility during the supply disruption and the patient surge.

2. The method of claim 1, further comprising entering into the computer one or more of healthcare product categories, healthcare product stock keeping units (SKUs), and the healthcare facility's usage rate of healthcare product stock keeping units (SKUs) to obtain the minimum healthcare product inventory required to support the healthcare facility during the supply chain disruption.

3. The method of claim 2, wherein the healthcare facility's usage rate of healthcare product SKUs is manually entered.

4. The method of claim 2, wherein the healthcare facility's usage rate of healthcare product SKUs is obtained upon entry of an identification number for the healthcare facility.

5. The method of claim 1, further comprising determining from the healthcare facility's usage rate of healthcare product SKUs different healthcare product SKUs having redundant functions and wherein the minimum healthcare product inventory required to support the healthcare facility during the supply chain disruption excludes at least one healthcare product SKU having a redundant function.

6. The method of claim 1, further comprising performing one or more of:
- obtaining a cost analysis of the recommended minimum healthcare product inventory;
- entering current healthcare facility inventory of supply chain healthcare products subject to supply disruption; and
- determining the difference between the recommended minimum healthcare product inventory and a current healthcare facility inventory of supply chain products subject to supply disruption, and obtaining a cost analysis of the recommended minimum healthcare product inventory required to bring supplies to the minimum level.

7. The method of claim 1, wherein the computer program is linked to an inventory system of the healthcare facility and a pricing system of a healthcare product supplier and, optionally, automatically places an order for healthcare products to bring the inventory to the recommended minimum healthcare product level.

8. The method of claim 1, wherein the assumptions related to the patient surge further include a number of beds in the healthcare facility.

9. The method of claim 8, further comprising obtaining from the computer program an estimate of a rate of increase in a number of patients admitted to the healthcare facility due to the pandemic disease outbreak.

10. The method of claim 9, further comprising performing one or more of:
- obtaining a cost analysis of the recommended minimum healthcare product inventory;
- entering current healthcare facility inventory of healthcare products; and
- determining a difference between recommended minimum healthcare product inventory and a current inventory of healthcare products, and obtaining a cost analysis of recommended minimum healthcare product inventory required to bring supplies to the recommended minimum product inventory.

11. The method of claim 10, wherein the computer program is linked to an inventory system of the healthcare facility and a pricing system of a healthcare products supplier and, optionally, automatically places an order for healthcare products to bring the inventory level to the recommended minimum healthcare product level.

12. The method of claim 1, wherein the disease is influenza.

13. A method of preparing a healthcare facility for a potential healthcare product supply chain disruption using a computer program executed by a computer having a processor, the method comprising:
- providing in the computer program a list comprising a list of healthcare continuity products, wherein the healthcare continuity products are selected based on typical usage by the healthcare facility, the healthcare continuity products including pharmaceuticals and non-pharmaceuticals;
- providing to the computer program assumptions affecting maintenance of an adequate supply of healthcare products during the potential supply disruption, the assumptions including an estimate of a population served by the healthcare facility and a period of time of the potential supply disruption; and
- executing the computer program using the processor to process the list of healthcare continuity products and assumptions related to the supply disruption to obtain a recommended minimum healthcare product inventory required to support the healthcare facility during the supply chain disruption.

14. The method of claim 13, further comprising entering into the computer healthcare product categories, healthcare product SKUs, a current inventory of healthcare products on hand at the healthcare facility, and the healthcare facility's usage rate of healthcare product stock keeping units (SKUs) to obtain the minimum healthcare product inventory required to support the healthcare facility during the supply chain disruption.

15. The method of claim 14, further comprising determining from the healthcare facility's usage rate of healthcare product SKUs different healthcare product SKUs having redundant functions and wherein the minimum healthcare product inventory required to support the healthcare facility during the supply chain disruption excludes at least one healthcare product SKU having redundant function.

16. A method of preparing a healthcare facility for a supply of healthcare products due to a patient surge due to a pandemic disease outbreak using a computer program executed by a computer having a processor, the method comprising:
- providing in the computer program a list comprising a list of surge preparedness pharmaceutical and non-pharmaceutical healthcare products, wherein at least a portion of the surge preparedness healthcare products are selected to treat symptoms and/or complications of a specified illness;
- on an input screen generated by the processor on the computer, providing to the computer program a set of assumptions related to the patient surge, the set of assumptions including a pandemic disease attack rate, a total population served by the healthcare facility, a hospitalization rate of the population based on the pandemic disease attack rate and a length of the pandemic disease outbreak; and
- executing the computer program using the processor to process the list of surge preparedness healthcare products and assumptions related to the patient surge to obtain a recommended minimum healthcare product inventory required to support the healthcare facility during the patient surge.

17. The method of claim 16, wherein the assumptions related the patient surge further include a number of beds in the healthcare facility.

18. The method of claim 17, further comprising obtaining from the computer program an estimate of a rate of increase in a number of patients admitted to the healthcare facility due to the pandemic disease outbreak.

19. The method of claim 18, further comprising entering healthcare product categories, healthcare product SKUs, a current inventory of healthcare products on hand at the healthcare facility, and the healthcare facility's usage rate of healthcare product stock keeping units (SKUs); and determining from the healthcare facility's usage rate of healthcare product SKUs to identify different healthcare product SKUs having redundant functions, and wherein the minimum healthcare product inventory required to support the healthcare facility during the pandemic disease outbreak excludes at least one healthcare product SKU having redundant function.

20. A system to assist a healthcare facility in preparing for a potential supply chain disruption, a patient surge, or both, comprising:
   a computer executing one or more applications;
   a database comprising a list of healthcare products; and
   an interface to the one or more applications through which assumptions relating to the supply chain disruption and the patient surge are entered into;
   wherein the assumptions include (i) a pandemic rate of attack, a total population served by the healthcare facility, a hospitalization rate of the population based upon the pandemic disease attack rate on the population and a length of a pandemic disease outbreak, and/or (ii) an estimate of a population served by the healthcare facility and a length of time of the potential supply chain disruption;
   wherein the computer processes the assumptions using a first list of pharmaceutical and non-pharmaceutical healthcare continuity products, wherein the healthcare continuity products are selected based on typical usage by the healthcare facility, and a second list of pharmaceutical and non-pharmaceutical surge preparedness healthcare products, wherein at least a portion of the surge preparedness healthcare products are selected to treat symptoms and/or complications of a specified illness;
   wherein the one or more applications recommend a minimum healthcare product inventory for products within the database based on the entered assumptions when the healthcare facility is involved in the supply chain disruption, the patient surge event, or both.

21. The system of claim 20, wherein the database contains a list of products which are routinely used by the healthcare facility and/or are products used to treat a symptom and/or complications of a specific illness.

22. The system of claim 20, wherein the one or more applications determines the minimum recommended inventory using one or more of healthcare product categories, healthcare product SKUs, a current inventory of healthcare products on hand at the healthcare facility, and the healthcare facility's usage rate of healthcare product stock keeping units (SKUs) to obtain the minimum healthcare product inventory required to support the healthcare facility during the supply chain disruption.

23. The system of claim 20, wherein the one or more applications determines the minimum recommended inventory using one or more of healthcare product categories, healthcare product SKUs, a current inventory of healthcare products on hand at the healthcare facility, and the healthcare facility's usage rate of healthcare product stock keeping units (SKUs); and one or more applications further determines from the healthcare facility's usage rate of healthcare product SKUs to identify different healthcare product SKUs having redundant functions, and wherein the minimum healthcare product inventory required to support the healthcare facility during the supply chain disruption excludes at least one healthcare product SKU having redundant function.

24. The system of claim 20, wherein the one or more applications determines the minimum recommended inventory using assumptions related a patient surge due to a pandemic disease outbreak, the assumptions further comprising a number of beds in the healthcare facility and hospitalization rate of the population based upon the pandemic disease attack rate on the population.

* * * * *